(12) United States Patent
Lin et al.

(10) Patent No.: US 10,985,070 B2
(45) Date of Patent: Apr. 20, 2021

(54) METHOD FOR FORMING NANO SENSING CHIP BY SELECTIVE DEPOSITION OF SENSING MATERIALS THROUGH DEVICE-LOCALIZED JOULE HEATING AND NANO SENSING CHIP THEREOF

(71) Applicant: NATIONAL CHIAO TUNG UNIVERSITY, Hsinchu (TW)

(72) Inventors: Ru-Zheng Lin, Jiji Township (TW); Jeng-Tzong Sheu, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 16/686,604

(22) Filed: Nov. 18, 2019

(65) Prior Publication Data

US 2020/0083105 A1    Mar. 12, 2020

Related U.S. Application Data

(62) Division of application No. 16/052,484, filed on Aug. 1, 2018.

(30) Foreign Application Priority Data

May 3, 2018   (TW) ................. 107115110

(51) Int. Cl.
*G01N 33/00*    (2006.01)
*H01L 21/28*    (2006.01)
(Continued)

(52) U.S. Cl.
CPC ....... *H01L 21/82345* (2013.01); *G01N 27/00* (2013.01); *G01N 33/0031* (2013.01);
(Continued)

(58) Field of Classification Search
CPC ......... H01L 21/82345; H01L 21/28556; H01L 27/1203; H01L 29/66742; H01L 29/78651; G01N 27/00; G01N 33/0031
(Continued)

(56) References Cited

U.S. PATENT DOCUMENTS 8,389,325 B2    3/2013 Carella et al.
2010/0181648 A1  7/2010 Lin et al.
(Continued)

OTHER PUBLICATIONS

Jin Huang and Qing Wan, Gas Sensors Based on Semiconducting Metal Oxide One-Dimensional Nanostructures, Dec. 4, 2009, www.mdpi.com/journal/sensors (Year: 2009).*

(Continued)

*Primary Examiner* — Didarul A Mazumder
(74) *Attorney, Agent, or Firm* — Birch, Stewart, Kolasch & Birch, LLP

(57) ABSTRACT

A method for forming a nanodevice sensing chip includes forming nanodevices having a sensing region capable of producing localized Joule heating. Individual nanodevice is electrical-biased in a chemical vapor deposition (CVD) system or an atomic layer deposition (ALD) system enabling the sensing region of the nanodevice produce localized Joule heating and depositing sensing material only on this sensing region. A sensing chip is formed via nanodevices with sensing region of each nanodevice deposited various materials separately. The sensing chip is also functioned under device Joule self-heating to interact and detect the specific molecules.

14 Claims, 13 Drawing Sheets
(6 of 13 Drawing Sheet(s) Filed in Color)

(51) Int. Cl.
*H01L 21/8234* (2006.01)
*H01L 21/285* (2006.01)
*H01L 29/66* (2006.01)
*H01L 29/786* (2006.01)
*G01N 27/00* (2006.01)
*H01L 27/12* (2006.01)

(52) U.S. Cl.
CPC .... *H01L 21/28556* (2013.01); *H01L 27/1203* (2013.01); *H01L 29/66742* (2013.01); *H01L 29/78651* (2013.01)

(58) Field of Classification Search
USPC .......................................... 257/253; 438/49
See application file for complete search history.

(56) References Cited

U.S. PATENT DOCUMENTS

| 2011/0133167 A1* | 6/2011 | Bangsaruntip .... H01L 29/66772 257/24 |
| 2014/0252306 A1* | 9/2014 | Du ........................ B82Y 10/00 257/9 |

OTHER PUBLICATIONS

Jin Huang and Qing Wan; "Gas Sensors Based on Semiconducting Metal Oxide One-Dimensional Nanostructures" Published: Dec. 4, 2009; Key Laboratory for Micro-Nano Optoelectronic Devices of the Ministry of Education and State KeyLaboratory of Chemo/Biosensing and Chemometrics, Hunan University, Changsha, 410082, China; E-Mail: huangjin8607@gmail.com; pp. 9903-9924.*

U.S. Appl. No. 16/052,484, filed Aug. 1, 2018.

Ahn et al., "Self-heated silicon nanowires for high performance hydrogen gas detection", Nanotechnology, 26 (9), 095501, 2015, pp. 1-10.

Chen et al., "Localized Joule Heating As a Mask-Free Technique for the Local Synthesis of ZnO Nanowires on Silicon Nanodevices", Nano Letters, 2011, 11, pp. 4736-4741.

Liu et al., "Enhancement of detection by selective modification of silicon nanobelt field-effect transistors via localized Joule heating", Sensors and Actuators B-Chemical, 192, pp. 111-116, 2014.

Liu et al., "Self Assembled Monolayer-Based Selective Modification on Polysilicon Nanobelt Devices", ACS Applied Materials & Interfaces, 5, 2013, pp. 10048-10053.

Park et al., "Selective Surface Functionalization of Silicon Nanowires via Nanoscale Joule Heating", Nano Letters, 2007, vol. 7, No. 10, pp. 3106-3111.

Tran et al., "Hydrogen gas sensors from polysilicon nanobelt devices selectively modified with sensing materials", Nanotechnology, 27, 505604, 2016, pp. 1-9.

Yun et al., "A self-heated silicon nanowire array: selective surface modification with catalytic nanoparticles by nanoscale Joule heating and its gas sensing applications", Nanoscale, 5 (15), pp. 6851-6856, 2013.

Zhang et al., "Self-assembled monolayer-assisted silicon nanowire biosensor for detection of protein-DNA interactions in nuclear extracts from breast cancer cell", Biosensors and Bioelectronics 2011, 26 (7), pp. 3233-3239.

* cited by examiner

METHOD FOR FORMING NANO SENSING CHIP BY SELECTIVE DEPOSITION OF SENSING MATERIALS THROUGH DEVICE-LOCALIZED JOULE HEATING AND NANO SENSING CHIP THEREOF

CROSS REFERENCE TO RELATED APPLICATIONS

This application is a Divisional of copending application Ser. No. 16/052,484, filed on Aug. 1, 2018, which claims priority under 35 U.S.C. § 119(a) to application Ser. No. 10/711,510, filed in Taiwan on May 3, 2018, all of which are hereby expressly incorporated by reference into the present application.

BACKGROUND OF THE INVENTION

1. Field of the Invention

The present invention generally relates to a method for forming a nano sensing chip. Particularly, the present invention relates to a method for forming a nano sensing chip by selective deposition of sensing materials through device-localized Joule heating and chemical vapor disposition (CVD) or atomic layer disposition (ALD) and a nano sensing chip thereof.

2. Description of the Prior Art

Because of their high sensitivity in response to changes in surface potential, nanodevices (e.g. nanowire (NW) field-effect transistors and nanobelt (NB) devices) have been developed for sensing applications. However, the nanodevices need specific modifications to exhibit significant selectivity toward target species.

Conventional surface modifications for nanodevices include: (1) evaporating or sputtering sensing materials through the shadow mask techniques, (2) physically or chemically adsorbing or bonding molecules with specific functional group onto the surface through the self-assembled monolayer (SAM) techniques, (3) utilizing localized Joule heating to ablate a region of polymer film on the nanodevice and evaporating or sputtering sensing materials through the lift-off processes, (4) utilizing localized Joule heating to grow sensing materials in solutions, or (5) utilizing localized Joule heating to ablate a region of the film on the nanodevice and forming a layer of sensing materials through the SAM techniques.

However, shadow mask techniques, SAM processes, and lift-off processes are very difficult to modify selectively only at specific regions of the device surface, especially when the device is further scaled down. As the devices become smaller and smaller, it is difficult to selectively evaporate or sputter materials only on the device channel by using shadow mask, so the chance of depositing materials outside the device channel is getting higher and higher, not feasible for low concentration sensing applications. Moreover, when depositing different materials on individual devices by the lift-off techniques, the processes of coating, ablating, lift-off, and evaporating or sputtering are repeated for different materials, and the ablating or lift-off processes will cause contaminations or peeling of the previously deposited materials, decreasing the sensitivity of the nanodevices for sensing applications or even resulting in devices fail.

SUMMARY OF THE INVENTION

It is an object of the invention to provide a method for forming a nano sensing chip by selective deposition of sensing materials on specific regions through localized Joule heating and the chemical vapor deposition (CVD) or the atomic layer deposition (ALD). The specific region is the most sensitive region of the device channel in response to changes in surface potential, so the method is suitable for manufacture of nanoscale sensing devices.

In an embodiment, the invention provides a method for forming a nano sensing chip. The method includes: forming a nanodevice having a region capable of producing localized Joule heating, and in a CVD system or an ALD system enabling the region of the nanodevice produce localized Joule heating and depositing a sensing material only on the region.

It is another object of the invention to provide a method for forming a nano sensing chip by sequentially electrical-biasing the nanodevices to selectively depositing different sensing materials on the sensing regions of different nanodevices through localized Joule heating and CVD or ALD, so as to simplify the manufacturing processes and prevent the previously deposited sensing materials from contamination or peeling.

In another embodiment, the invention provides a method for forming a nano sensing chip. The method includes: forming a plurality of nanodevices into a first group and a second group, each of the first group or the second group including at least one of the plurality of nanodevices, each of the plurality of nanodevices having a sensing region capable of producing localized Joule heating; in a CVD system or an ALD system enabling the sensing region of the at least one nanodevice in the first group produce localized Joule heating and depositing a first sensing material only on the sensing region of the at least one nanodevice in the first group; and after the first sensing material is deposited, enabling the sensing region of the at least one nanodevice in the second group produce localized Joule heating and depositing a second sensing material only on the sensing region of the at least one nanodevice in the second group, wherein the at least one nanodevice in the second group is different from the at least one nanodevice in the first group, and the second sensing material is different from the first sensing material.

It is yet another object of the invention to provide a nano sensing chip, which consists of multiple nanodevices with various sensing materials. Each of the nanodevices can function under device Joule self-heating at appropriate working temperature. The nano structure (e.g. nanowire or nanobelt) Joule self-heating can effectively reduce the power consumption during sensing operation and can be applied to sensing applications of multiple gases in comparison to conventional gas-sensing techniques requiring additional heat source and larger power consumption.

In another embodiment, a nano sensing chip of the invention includes a plurality of nanodevices divided into a first group and a second group, each of the first group and the second group including at least one of the plurality of nanodevices, each nanodevice including a source, a drain, and a device channel with two ends electrically connecting the source and the drain, the device channel including a lightly-doped region; a first sensing material deposited on the lightly-doped regions of the at least one nanodevice in the first group; and a second sensing material deposited on the lightly-doped region of the at least one nanodevice in the second group, wherein the at least one nanodevice in the second group is different from the at least one nanodevice in the first group, and the second sensing material is different from the first sensing material.

Compared to the conventional techniques, the method of the invention utilizes localized Joule-heating to selectively deposit sensing materials on specific regions through CVD or ALD, which is suitable for manufacturing nano sensing chips. Moreover, the method of the invention further selectively deposits various sensing materials on the sensing regions of different nanodevices by sequentially electrical-biasing the nanodevices, so the manufacturing processes are simplified, and contamination or peeling of the previously deposited sensing materials is also prevented. Moreover, the nano sensing chip of the invention has various sensing materials deposited on different nanodevices in a same chip, so the nano sensing chip of the invention is suitable sensing applications of multiple gases and is able to function under device Joule self-heating, superior in portable gas sensing applications.

BRIEF DESCRIPTION OF THE DRAWINGS

The patent or application file contains at least one color drawing. Copies of this patent or patent application publication with color drawing will be provided by the USPTO upon request and payment of the necessary fee.

DETAILED DESCRIPTION OF THE PREFERRED EMBODIMENT

The present invention provides a method for forming a nano sensing chip, particularly a method for forming a nano sensing chip by selective deposition of sensing materials through device-localized Joule heating and CVD or ALD, so the method of the invention can be applied to the manufacture of nanodevices or prevent contamination or peeling of previously deposited materials, but not limited thereto. Hereinafter, embodiments of the invention will be described in detail with reference to the drawings.

Figure 1A:
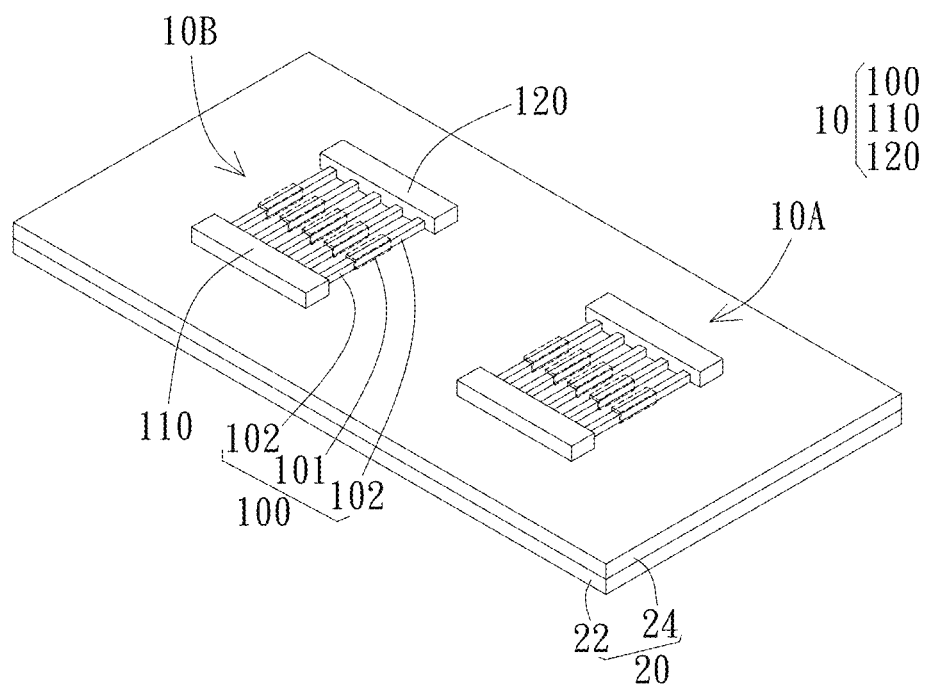
FIG. 1A is a schematic view of an embodiment of nanodevices.
Figure 1B:
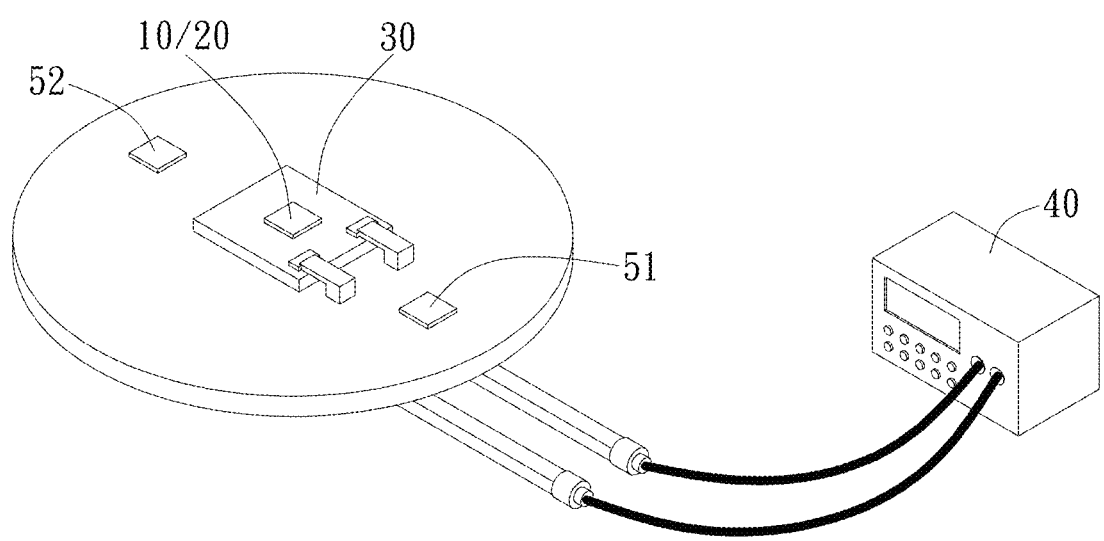
FIG. 1B is a schematic side view of an embodiment of selective deposition of sensing materials on nanodevices through localized Joule heating in a CVD or ALD system.

As shown in FIG. 1A and FIG. 1B, in an embodiment, the method of forming a nano sensing chip includes forming a nanodevice 10 having a region (such as 101) capable of producing localized Joule heating; and in a CVD system or an ALD system enabling the region of the nanodevice 10 produce localized Joule heating and depositing a sensing material only on the region (such as 101).

Specifically, as shown in FIG. 1A, the step of forming the nanodevice 10 includes forming a device channel 100 having a lightly-doped region 101, and the lightly-doped region 101 is the region capable of producing localized Joule heating. The nanodevice 10 further includes a source 110 and a drain 120. Two ends of the device channel 100 electrically connecting the source 110 and the drain 120. In an embodiment, the device channel 100 preferably further includes two heavily-doped regions 102. The two heavily-doped regions 102 are disposed at two ends of the lightly-doped region 101 and adjoin the source 110 and the drain 120, respectively. In an embodiment, the device channel 100 includes a semiconductor material, and the device channel 100 can be a nanobelt or a nanowire, but not limited thereto. In another embodiment, the device channel 100 can include any semiconductor materials as appropriate. According to practical applications, the doped region can be an n-doped region or a p-doped region. In an embodiment, the nanodevice 10 can be a $n^+/n^-/n^+$ doped dual junction nanodevice. For example, the nanodevice can include three doped regions: a 2 μm long $n^-$ region (e.g. 101) in the middle and two 5.5 μm long $n^+$ regions (e.g. 102) at two distal ends, but not limited thereto. In another embodiment, the nanodevice 10 can be a $p^+/p^-/p^+$ doped dual junction poly or single crystalline nanodevice, and the length of each doped region can be modified according to design needs. In an embodiment, the lightly-doped region 101 preferably has a doping dosage less than $1 \times 10^{14}/cm^2$, and the heavily-doped region preferably has a doping dosage larger than $1 \times 10^{15}/cm^2$. Therefore, the power dissipation at $n^-$ region is relatively larger, and the $n^-$ region is capable of producing localized Joule heating. That is, the lightly-doped region 101 is the region capable of producing Joule heating of the nanodevice 10. For example, n typed dopant preferably includes phosphorous or arsenic, and the doping dosage of the $n^-$ region is preferably $8 \times 10^{13}/cm^2$, and the doping dosage of the $n^+$ region is preferably $3 \times 10^{15}/cm^2$. The resistance of the $n^-$ region and the $n^+$ region is 30.3 and 6.06 kΩ, respectively, so the power dissipation at the $n^-$ region is at least 5-fold larger than that at the $n^+$ region.

As shown in FIG. 1A, the step of forming the nanodevice includes forming a plurality of the nanodevices. Specifically, the plurality of nanodevices 10 are formed on a substrate 20 in an array arrangement. For example, the substrate 20 is preferably a semiconductor substrate or a semiconductor on insulator substrate, such as silicon substrate or silicon on insulator substrate. In this embodiment, the plurality of nanodevices 10 are formed on the substrate 20 having an insulation layer (e.g. oxide layer) 24 stacked on a silicon substrate 22, but not limited thereto. The plurality of nanodevices 10 are preferably divided in several groups according to sensing materials to be deposited thereon, so each group of nanodevice(s) 10 can be independently electrical-biased. For example, the plurality of nanodevices can be divided into a first group 10A and a second group 10B. Each of the first group 10A and the second group 10B includes at least one nanodevice 10, e.g. five nanodevices in each group in this embodiment, but not limited thereto. In the same group, the device channels 100 are preferably connected to a common source 110 and a common drain 120, so the nanodevices 10 in the same group can be effectively controlled at the same time. It is noted that each group includes at least one nanodevice, and the number of nanodevices in each group can be the same or different. Moreover, for a same sensing material, the plurality of nanodevices can be divided into one or more than one group according to practical applications.

As shown in FIG. 1B, the substrate 20 with the nanodevices formed thereon is placed in a CVD system or an ALD system. The nanodevices 10 are connected to an external power supply 40 through a printed circuit board 30 and wires. Specifically, the power supply 40 and the printed circuit board 30 can control the bias voltage applied to the nanodevice 10, so the lightly-doped region 101 of the nanodevice 10 can produce localized Joule heating, and the sensing material (indicated by dotted lines in FIG. 1A) is deposited on the lightly-doped region 101 of the nanodevice 10. For example, when applying the bias voltage to the nanodevice 10 to enable the lightly-doped region 101 produce localized Joule heating and increase the temperature of the lightly-doped region 101, the reaction gas(es) is introduced through the gas inlet 51, so the sensing material can be deposited only on the lightly-doped region 101 of the nanodevice 10 through CVD or ALD, and the residual gas(es) is exhausted through the gas outlet 52. It is noted that the temperature of the lightly-doped region 101 can be controlled by controlling the bias voltage applied to the nanodevice 10 through the power supply 40, and the thickness of the sensing material deposited on the lightly-doped region 101 can be controlled by controlling the number of deposition cycles (or the deposition time) and the bias voltage (the deposition temperature).

Moreover, when multiple sensing materials are to be deposited on the nanodevices, by controlling the bias voltage applied to individual nanodevices, various sensing materials can be sequentially and selectively deposited on different nanodevices. In an embodiment, the step of enabling the region produce localized Joule heating includes: enabling the region of the nanodevice in the first group 10A produce localized Joule heating to deposit the sensing material (e.g. the first sensing material 210 of FIG. 9A) only on the region of the nanodevice 10 in the first group 10A. Specifically, only the nanodevices 10 in the first group 10A are electrical-biased through the power supply 40 and the printed circuit board 30, so the lightly-doped regions 101 of the device channels 100 of the nanodevices 10 in the first group 10A produce localized Joule heating, and the sensing material (e.g. the first sensing material 210 of FIG. 9A) is deposited only on the lightly-doped regions 101 of the nanodevices 10 in the first group 10A. For example, when the nanodevices 10 in the first group 10A are electrical-biased enabling the lightly-doped regions 101 thereof produce localized Joule heating and increase the temperature of the lightly-doped regions 101, the reaction gas is introduced through the gas inlet 51, and the first sensing material 210 is deposited only on the lightly-doped regions 101 of the nanodevices 10 in the first group 10A through plasmas-enhanced CVD (PECVD) or plasmas-enhanced ALD (PEALD) to achieve selective deposition of the first sensing material 210.

The method of the invention further includes: enabling the regions of the nanodevices 10 in the second group 10B produce localized Joule heating to deposit another sensing material (e.g. the second sensing material 220 of FIG. 9A) different from the first sensing material only on the regions of the nanodevices in the second group 10B. The nanodevices 10 in the second group 10B are different from the nanodevices 10 in the first group 10A. For example, after the first sensing material 210 is deposited, only the nanodevices 10 in the second group 10B are electrical-biased through the power supply 40 and the printed circuit board 30, so the lightly-doped regions 101 of the device channels 100 of the nanodevices 10 in the second group 10B produce localized Joule heating, and the sensing material (e.g. the second sensing material 220 of FIG. 9A) is deposited only on the lightly-doped regions 101 of the nanodevices 10 in the second group 10B. For example, when the nanodevices 10 in the second group 10B are electrical-biased enabling the lightly-doped regions 101 thereof produce localized Joule heating and increase the temperature of the lightly-doped regions 101, another reaction gas is introduced through the gas inlet 51, and the second sensing material 220 is deposited only on the lightly-doped regions 101 of the nanodevices 10 in the second group 10B through PECVD or PEALD to achieve selective deposition of the second sensing material 220.

In the embodiment, the first sensing material 210 and the second sensing material 220 can be metal materials or metal oxide semiconductor materials. In an embodiment, the metal material can be selected from the group consisting of platinum, palladium, tungsten, and iridium, but not limited thereto. The metal oxide semiconductor materials can be selected from the group consisting of tin oxide, zinc oxide, tungsten oxide, aluminum oxide, and hafnium oxide, but not limited thereto. Hereinafter, in an embodiment, the method of the invention is illustrated by selectively depositing Pt and ZnO through device-localized Joule heating and PEALD.

Specifically, when Pt is deposited on the lightly-doped regions 101 of the nanodevices 10 in the first group 10A by PEALD, the nanodevices 10 in the first group 10A are electrical-biased enabling the lightly-doped regions 101 thereof produce localized Joule heating. Precursors of Pt (e.g. MeCpPtMe3, Trimethyl-(methylcyclopentadienyl) Platinum) are introduced into the reaction chamber, and then $O_2$ plasmas treatment is performed. Consequently, Pt is selectively deposited only on the lightly-doped regions 101 of the nanodevices 10 in the first group 10A. Next, when ZnO is deposited on the lightly-doped regions 101 of the nanodevices 10 in the second group 10B by PEALD, the nanodevices 10 in the second group 10B are electrical-biased enabling the lightly-doped regions 101 thereof produce localized Joule heating. Precursors of ZnO (e.g. diethylzinc, DEZ) are introduced into the reaction chamber, and then O$_2$ plasmas treatment is performed. Consequently, ZnO is selectively deposited only on the lightly-doped regions 101 of the nanodevices 10 in the second group 10B. It is noted that the sensing materials can be selected according to practical applications, and the precursors can be selected according to sensing materials, so different sensing materials can be deposited on different nanodevices in the same chip, not limited to the embodiments.

Figure 2:
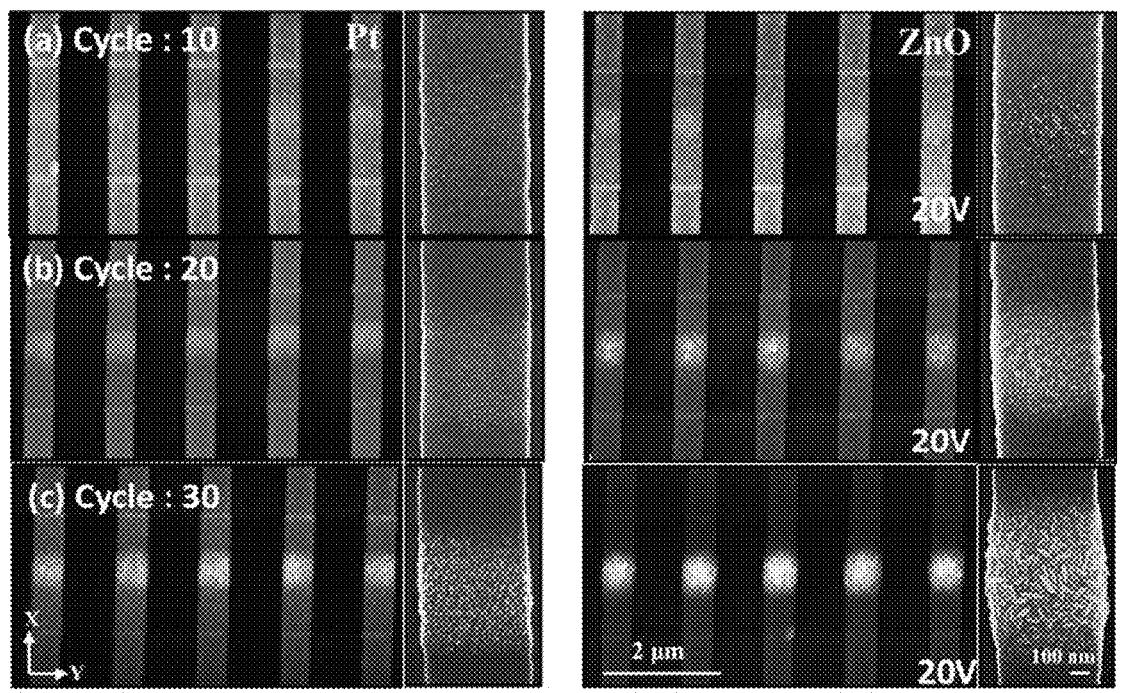
FIG. 2 presents atomic force microscopy (AFM) and top-view scanning electron microscopy (SEM) images after ALD (or CVD) for selective deposition of Pt and ZnO on the lightly-doped region of the nanodevice channel for various numbers of deposition cycles, (a) 10 cycles, (b) 20 cycles, and (c) 30 cycles.

FIG. 2 presents AFM and SEM images after ALD (or CVD) for selective deposition of Pt and ZnO on the n$^-$ region of the device channel for various numbers of deposition cycles, (a) 10 cycles, (b) 20 cycles, and (c) 30 cycles. As shown in FIG. 2, under a bias of 20 V and after 10 cycles of deposition, both Pt and ZnO nanoclusters are formed on the surface of the n$^-$ region of the device channel. When the number of deposition cycles increases to 20 and 30, the aggregation of the Pt and ZnO nanoclusters is intensified, and the deposited thickness is increased.

Figure 3:
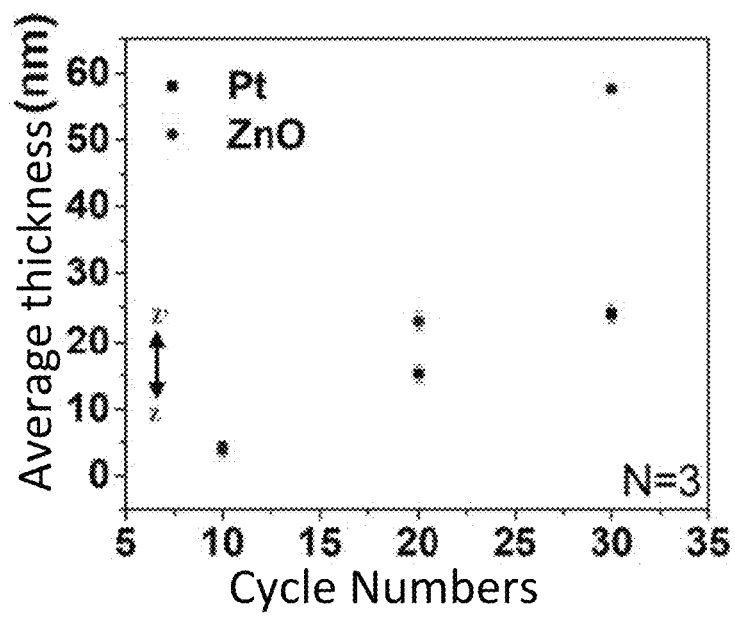
FIG. 3 shows average thicknesses of Pt and ZnO after various numbers of deposition cycles.
Figure 4:
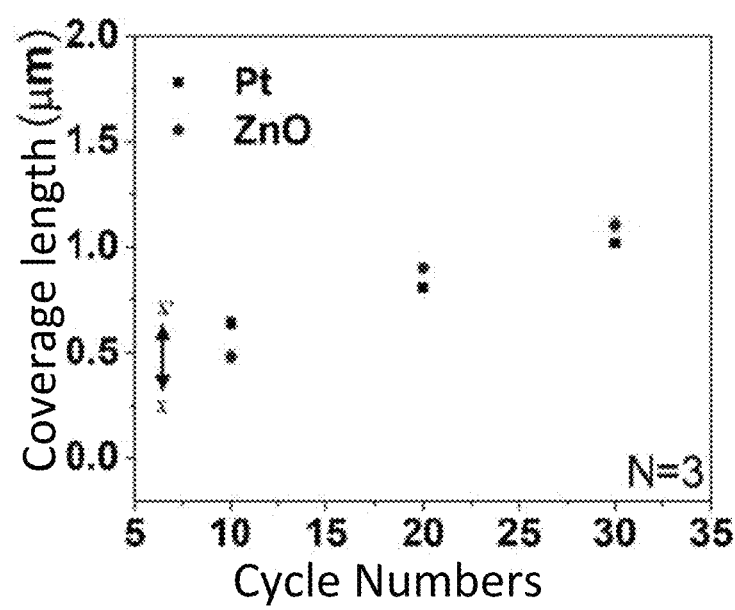
FIG. 4 shows average coverage lengths of Pt and ZnO after various numbers of deposition cycles.

Moreover, AFM can also be used to characterize the material average thickness and average coverage in the n$^-$ region. As shown in FIG. 3, for Pt, the average thickness is 3.85±1.1 nm after 10 cycles, 15.23±1.23 nm after 20 cycles, and 24.12±1.02 nm after 30 cycles, wherein the growth per cycle (GPC) is 8.04 Å/cycle. For ZnO, the average thickness is 4.12±0.83 nm after 10 cycles, 23.12±1.27 nm after 20 cycles, and 57.64±0.82 nm after 30 cycles, wherein the GPC is 19.21 Å/cycle. As shown in FIG. 4, for Pt, the average coverage length is 0.656±0.03 m after 10 cycles, 0.734±0.02 µm after 20 cycles, and 0.97±0.02 µm after 30 cycles. For ZnO, the average coverage length is 0.48±0.03 µm after 10 cycles, 0.694±0.02 µm after 20 cycles, and 1.103±0.03 µm after 30 cycles. Under substantial identical deposition conditions, the deposition rate of ZnO is 2.3 times faster than that of Pt, so the size of ZnO nanoclusters is greater than that of Pt nanoclusters.

Figure 5:
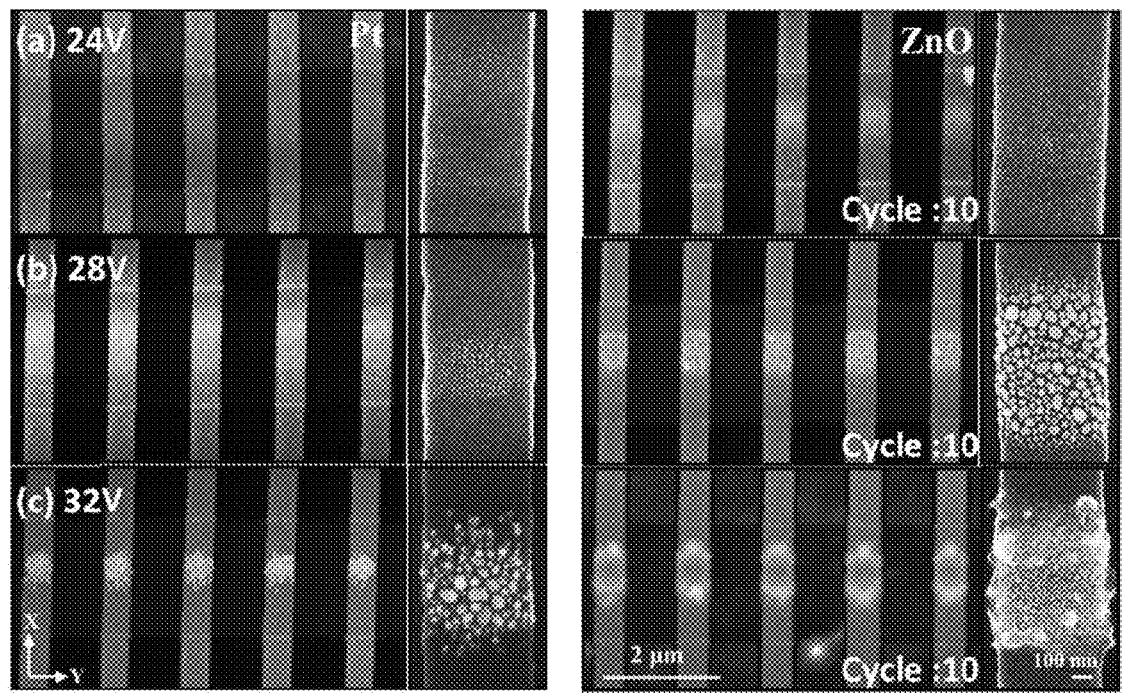
FIG. 5 presents AFM and SEM images after ALD (or CVD) for selective deposition of Pt and ZnO through a given number of deposition cycles on the lightly-doped region of the nanodevice channel under various bias voltages, (a) 24V, (b) 28V, and (c) 32V.
Figure 6:
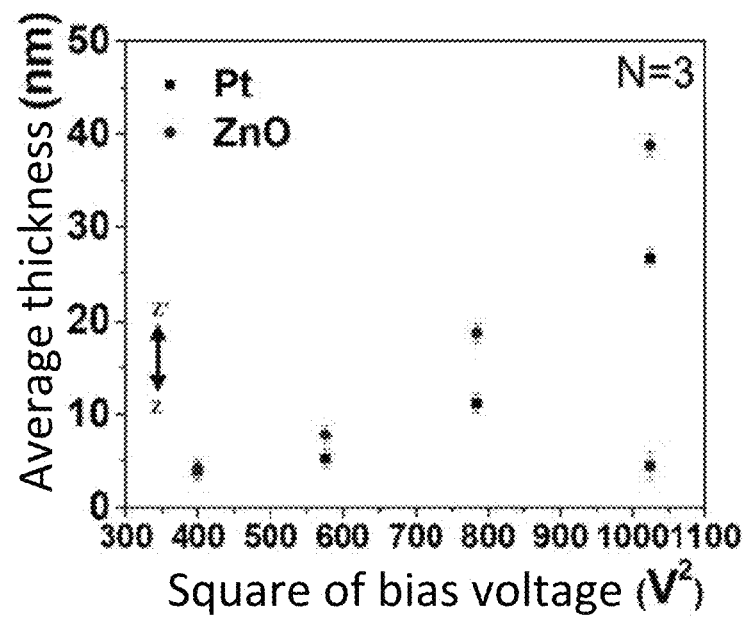
FIG. 6 shows average thicknesses of Pt and ZnO under various bias voltages.
Figure 7:
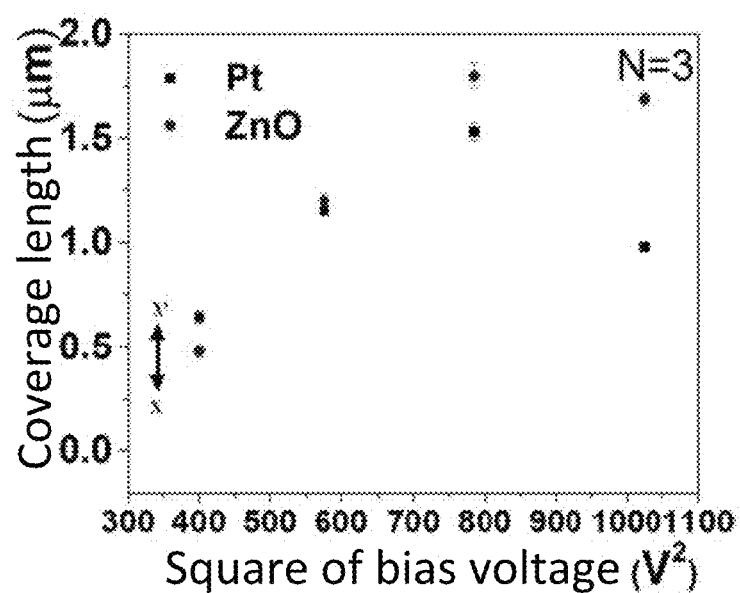
FIG. 7 shows average coverage lengths of Pt and ZnO under various bias voltages.

FIG. 5 presents AFM and SEM images after ALD (or CVD) for selective deposition of Pt and ZnO through a given number of deposition cycles on the lightly-doped region of the device channel under various bias voltages, (a) 24V, (b) 28V, and (c) 32V. As shown in FIG. 5, the given number of deposition cycles is 10 cycles. Agglomeration of the nanoclusters becomes evident upon increasing the temperature in the n$^-$ region. As shown in FIG. 6, for Pt, the average thickness is 5.18±1.01 nm at 24V, 11.2±1.01 nm at 28V, and 26.7±1.02 nm at 32V. For ZnO, the average thickness is 7.8±1.02 nm at 24V, 18.8±1.02 nm at 28V, and 38.8±1.23 nm at 32V at the two sides, as well as 4.4±1.02 nm at the middle of n$^-$ region. As shown in FIG. 7, for Pt, the average coverage length is 1.09±0.02 µm at 24V, 1.36±0.04 µm at 28V, and 0.88±0.02 µm at 32V. For ZnO, the average coverage length is 1.14±0.03 µm at 24V, 1.437±0.06 µm at 28V, and 0.9±0.03 µm at 32V. The average coverages reach their maxima for the selective depositions of both Pt and ZnO under a bias of 28V. At a bias of 32V, the high device surface temperature results in high mobility, such that the average coverage of Pt is lower, but larger nanoclusters are formed in the middle of the n$^-$ region.

Figure 8:
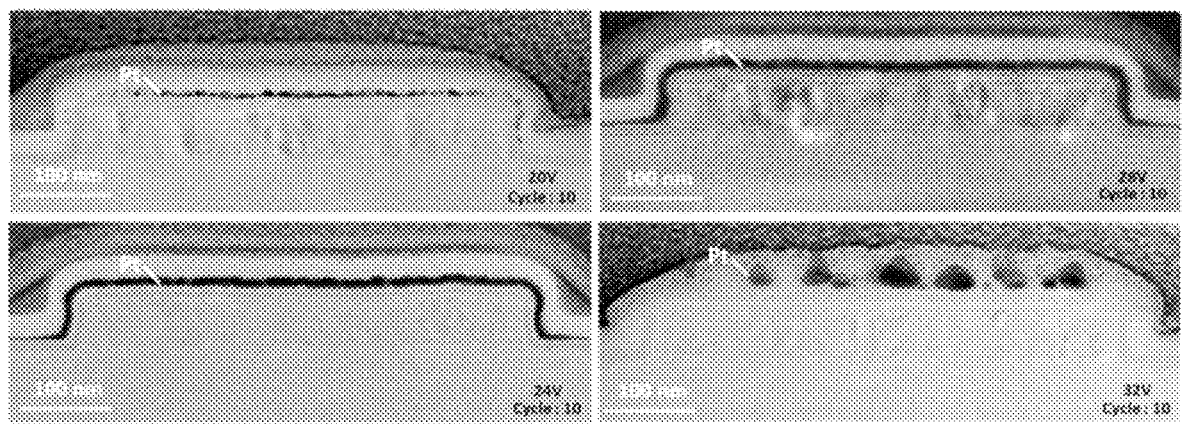
FIG. 8 presents cross-sectional TEM images of nanodevices after selective deposition Pt through a given number of deposition cycles under various bias voltages (20V, 24V, 28V, and 32V)

FIG. 8 presents cross-sectional TEM images of nanodevices after selective deposition through a given number of deposition cycles under various bias voltages (20V, 24V, 28V, and 32V). As shown in FIG. 8, the lightly-doped region of the silicon nanodevice is completely covered by a thin Pt layer when the Joule heating power is 24V or 28V, forming trigate-like structures (e.g. shown in bottom left and upper right). For Joule heating biases of 20V and 32V, the silicon device channel is covered by Pt nanoparticles, rather than thin films (e.g. shown in upper left and bottom right). At low bias and cycle number (e.g. 24V, 10 cycles), similar trigate-like surface coverage is shown after the selective deposition of Pt and ZnO.

Figure 9A:
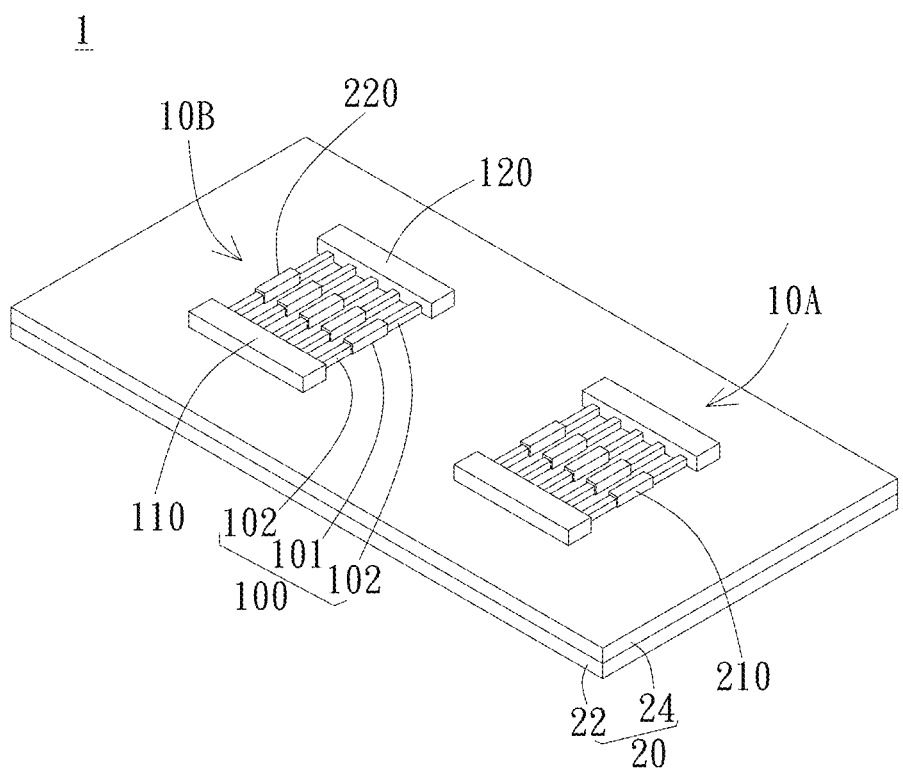
FIGS. 9A and 9B are a schematic view and a cross-sectional view of an embodiment of the nano-sensing chip of the invention.
Figure 9B:
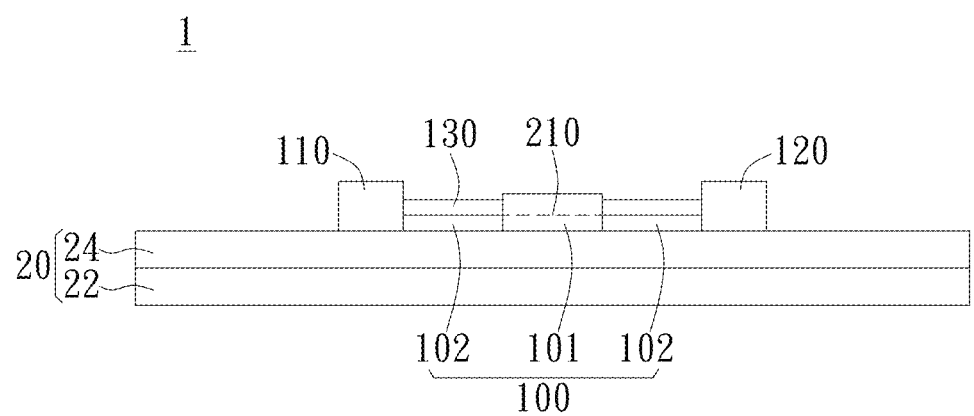

Furthermore, the method of the invention can be employed for applications of nano sensing chips, such as nano gas sensing chip, so various sensing materials can be deposited on individual nanodevices in a same chip, which can be applied to sensing applications of multiple target gases. The nano sensing chip can also function under device Joule self-heating, so as to effectively reduce the sensing power consumption. When the nanodevices are adopted in the nano sensing chip, nanobelts or nanowires can serve as the sensing regions or the device channels of the nanodevices. As shown in FIG. 9A and FIG. 9B, in an embodiment, the nano sensing chip 1 of the invention includes a plurality of nanodevices 10, a first sensing material 210, and a second sensing material 220. Each nanodevice 10 includes a source 110, a drain 120, and a device channel 100 with two ends electrically connecting the source 110 and the drain 120. The device channel 100 includes a lightly-doped region 101. The first sensing material 210 is deposited on the lightly-doped regions 101 of the nanodevices 10 in the first group 10A. The second sensing material 220 is deposited on the lightly-doped regions 101 of the nanodevices 10 in the second group 10B. The nanodevices 10 in the second group 10B are different from the nanodevices 10 in the first group 10A, and the second sensing material 220 is preferably different from the first sensing material 210.

Specifically, the arrangement of the plurality of nanodevices is similar to the arrangement in FIG. 1A. For example, the plurality of nanodevices 10 can be divided into several groups according to the sensing materials, and each group of nanodevices can be independently operated, so the first sensing material 210 and the second sensing material 220 are targeted to different gas molecules. For example, the plurality of nanodevices 10 are divided into the first group 10A and the second group 10B based on the first sensing material 210 and the second sensing material 220, respectively. Each of the first group 10A and the second group 10B includes at least one nanodevice 10 (e.g. five nanodevices). In an embodiment, the device channels 100 of the nanodevices 10 in the first group 10A or the second group 10B are parallel to each other, and adjacent device channels 100 are preferably spaced apart by a distance equal to or larger than 1 µm, but not limited thereto. In a same group, the device channels 100 of nanodevices 10 are preferably connected to a common source 110 and a common drain 120, so the temperature of the nanodevices in the same group can be effectively controlled at the same time, but not limited thereto.

Furthermore, the structure of each nanodevice 10 is similar to the structure in FIG. 1A. For example, the device channel 100 can be a n$^-$/n$^-$/n$^+$ or p$^+$/p$^-$/p$^+$ doped dual junction poly or single crystalline device channel. The doping dosage of the lightly-doped region is preferably less than $1 \times 10^{14}/cm^2$, and the doping dosage of the heavily-doped region is preferably larger than $1 \times 10^{15}/cm^2$, so the power dissipation at n$^-$ region is relatively larger, and the n$^-$ region is capable of producing localized Joule heating, but not limited thereto. It is noted the details of nanodevice can refer to the related descriptions of FIG. 1A and will not be elaborated again.

As shown in FIG. 9B, each nanodevice 10 further includes a dielectric layer 130. The dielectric layer 130 is disposed between the device channel 100 and the first sensing material 210 (or the second sensing material 220). In an embodiment, the dielectric layer 130 can be a singlelayered structure of oxide or nitride (e.g. SiO$_2$ or Si$_3$N$_4$). In another embodiment, the dielectric layer 130 can be a dual-layered structure including oxide and nitride. For example, a stack of silicon dioxide and silicon nitride can be formed on the silicon device channel as the dielectric layer 130.

The first sensing material 210 and the second sensing material 220 can be selectively deposited through localized Joule heating and PECVD or PEALD as described above. For example, by sequentially electrical-biasing the nanodevices 10 in the first group 10A and the nanodevices 10 in the second group 10B, the first sensing material 210 is deposited on the dielectric layer 130 corresponding to the lightly-doped regions 101 of the nanodevices 10 in the first group 10A, and the second sensing material 220 is deposited on the dielectric layer 130 corresponding to the lightly-doped regions 101 of the nanodevices 10 in the second group 10B. That is, the first sensing material 210 and the second sensing material 220 are formed on the dielectric layer 120 and correspond to the lightly-doped regions 101 of the nanodevices 10 in the first group 10A and the second group 10B, respectively. As described above, the first sensing material 210 and the second sensing material 220 are independently a metal material or a metal oxide semiconductor material. For example, the metal material can be selected from the group consisting of platinum, palladium, tungsten, and iridium, and the metal oxide semiconductor material can be selected from the group consisting of tin oxide, zinc oxide, tungsten oxide, aluminum oxide, and hafnium oxide, but not limited thereto. In an embodiment, the first sensing material 210 can be Pt, and the second sensing material 220 can be ZnO, which are configured to detect specific molecules, such as hydrogen and oxygen. It is noted that the sensing material can be selected based on the target gas and is not limited to the metal materials or the metal oxide materials in the embodiment.

Figure 10A:
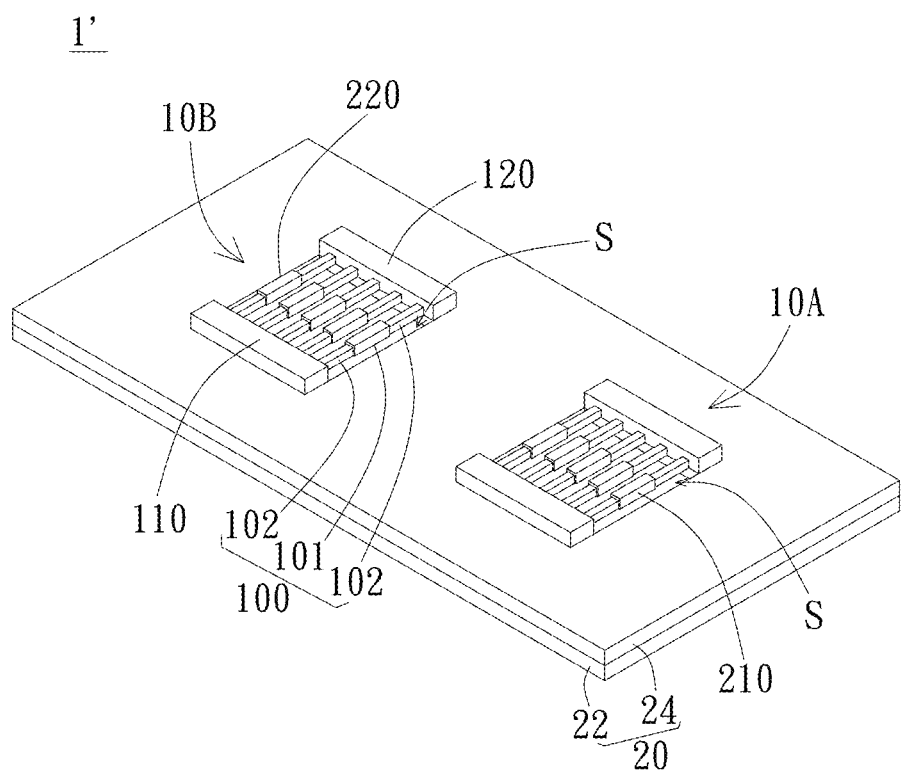
FIGS. 10A and 10B are a schematic view and a cross-sectional view of another embodiment of the nano-sensing chip of the invention.
Figure 10B:
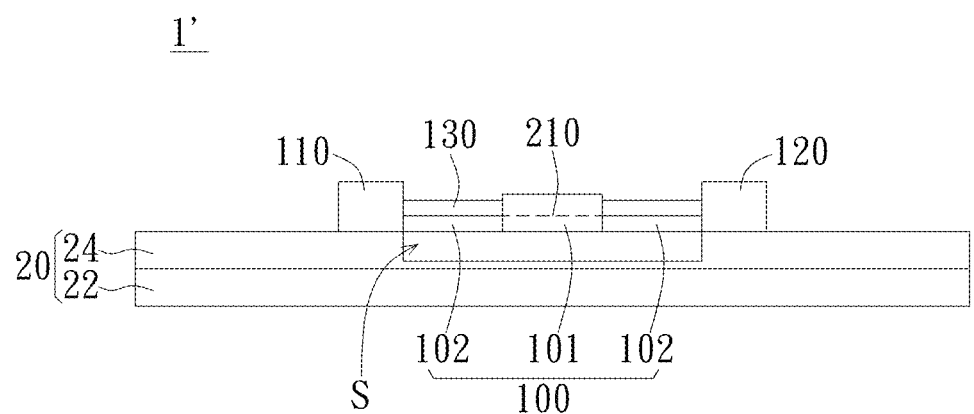
Figure 11A:
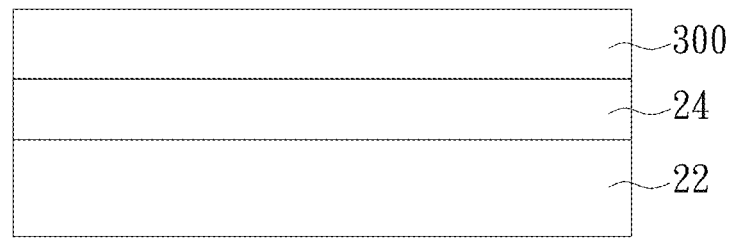
FIG. 11A to FIG. 11I are schematic views of an embodiment of the method of forming the nanodevice of the invention.
Figure 11B:
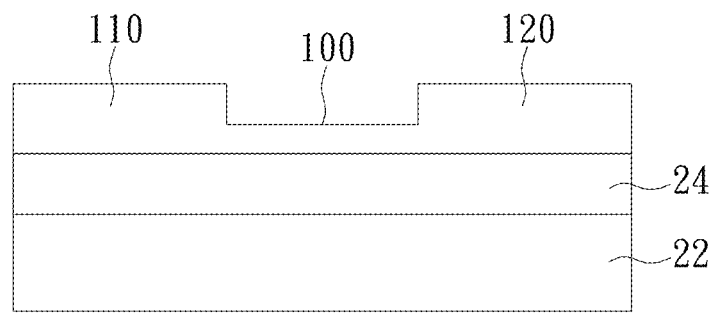
Figure 11C:
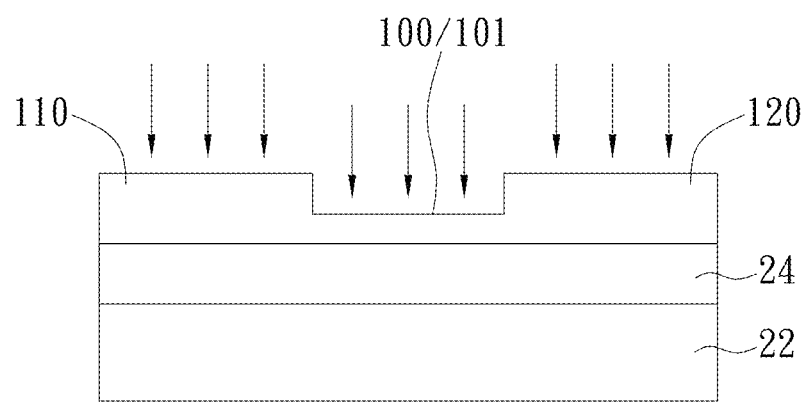
Figure 11D:
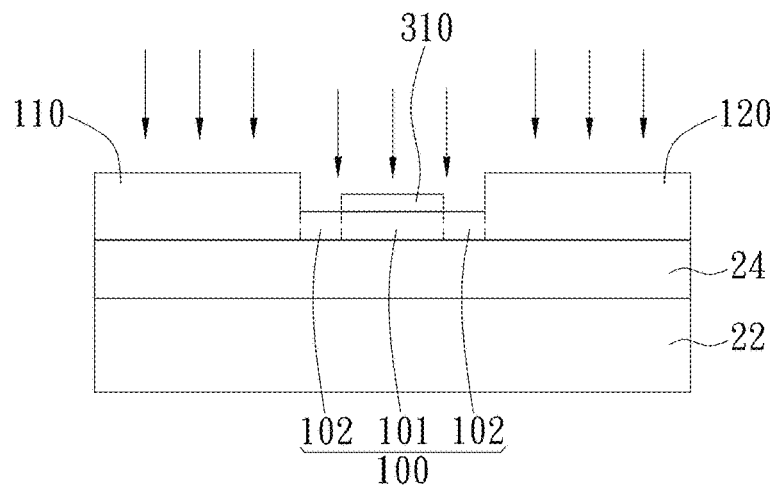
Figure 11E:
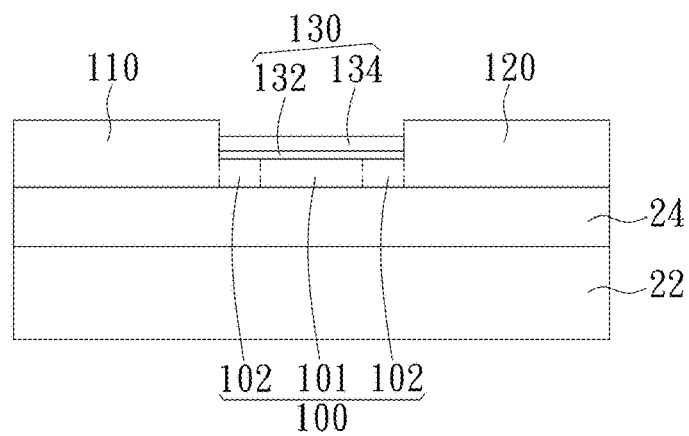

In another embodiment, as shown in FIG. 10 A and FIG. 10B, the nano sensing chip 1' includes a plurality of suspending nanodevices having a gap S between the device channel and the substrate. In an embodiment, the gap S between the device channel 100 and the substrate 20 is preferably equal to or larger than 7 µm, and adjacent device channels 100 are preferably spaced apart by a distance preferably equal to or larger than 7 µm, so the nanodevices can have a three-dimensional reaction with the surrounding gases. The suspending nanodevices can be formed by semiconductor manufacturing processes, such as deposition, lithography, etching, ion implantation. Then, the sensing materials are selectively deposited through localized Joule heating and CVD or ALD as described above. In an embodiment, as shown in FIG. 11A, an insulation layer 24 is formed on a silicon substrate 22, and a semiconductor active layer 300 is formed on the insulation layer 24. For example, a 7000 nm oxide layer is formed on the silicon wafer, and a 70 nm silicon layer is formed on the oxide layer. As shown in FIG. 11B, the active layer 300 is patterned to define the nanodevice. For example, the silicon layer is patterned by the processes, such as lithography, etching, to define the patterns of source 110, drain 120, and device channel 100. As shown in FIG. 11C, a first implantation is performed to form the lightly-doped region 101. Specifically, the first implantation with a dose of $3\times10^{13}$/cm$^2$ is performed on the source 110, the drain 120, and the device channel 100. As shown in FIG. 11D, a second implantation is performed to form heavily-doped regions 102 at two sides of the lightly-doped region 101. For example, after the first implantation, photoresist 310 masks the lightly-doped region 101, and the second implantation with a dose of $5\times10^{15}$/cm$^2$ is performed on the unmasked regions (e.g. source 110, drain 120). It is noted that FIG. 11D shows the photoresist 310 partially masks the device channel 100 as the lightly-doped region 101; however, in other embodiments, the photoresist 310 can mask the entire device channel 100 as the lightly-doped region 101, and the source 110 and the drain 120 serve as the heavily-doped regions at two sides of the lightly-doped region 101. As shown in FIG. 11E, a dielectric layer 130 is formed on the device channel 100. For example, after the second implantation, the photoresist 310 is removed, and a 5 nm oxide layer 132 and a 10 nm nitride layer 134 are sequentially formed on the device channel 100. It is noted that when the step of FIG. 11E is completed, the non-suspending nanodevice (e.g. the nanodevice 10 in FIG. 1A) is formed. The suspending nanodevice can be formed through the steps in FIG. 11F to FIG. 11I.

Figure 11F:
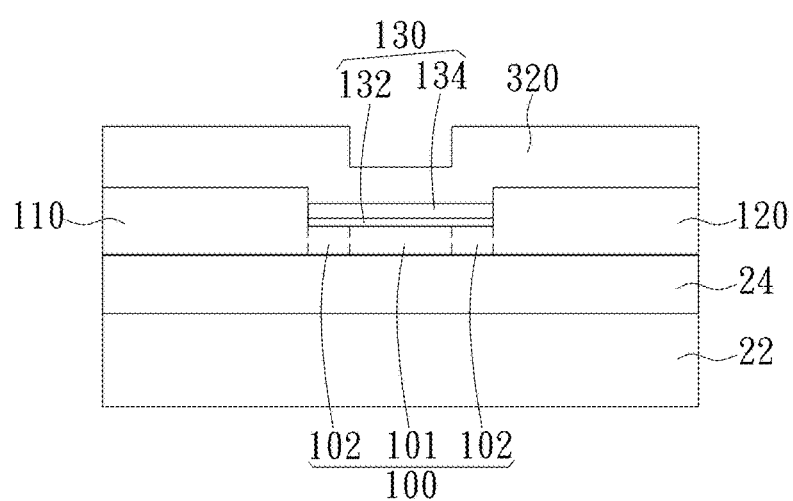
Figure 11G:
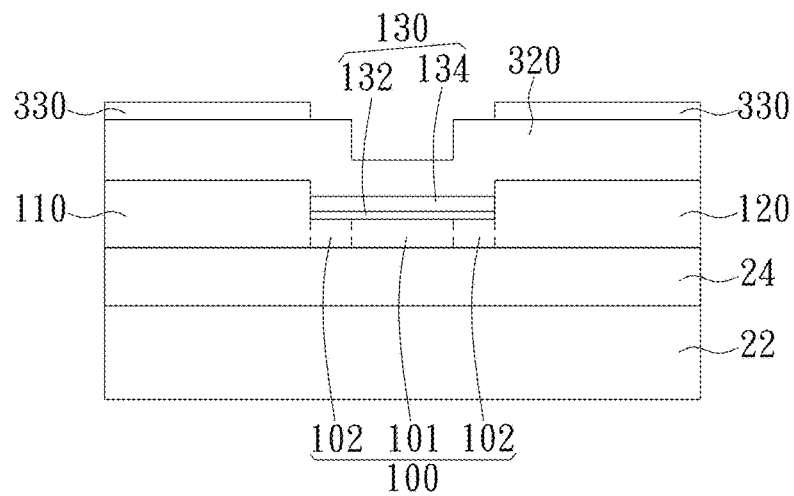
Figure 11H:
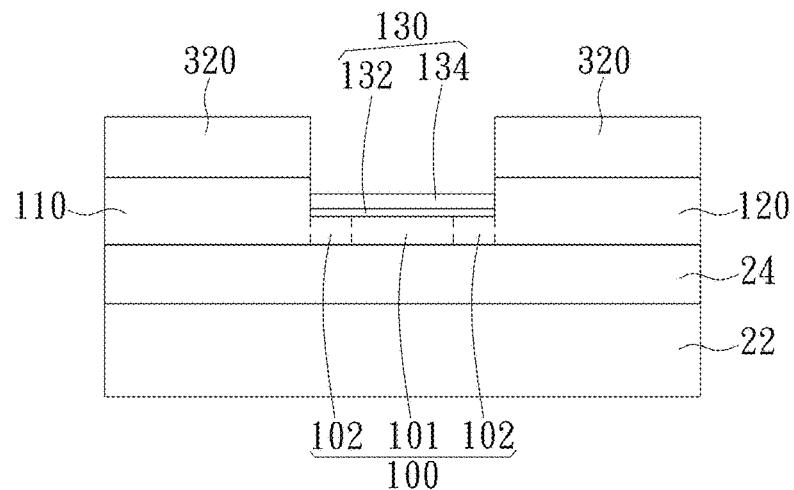
Figure 11I:
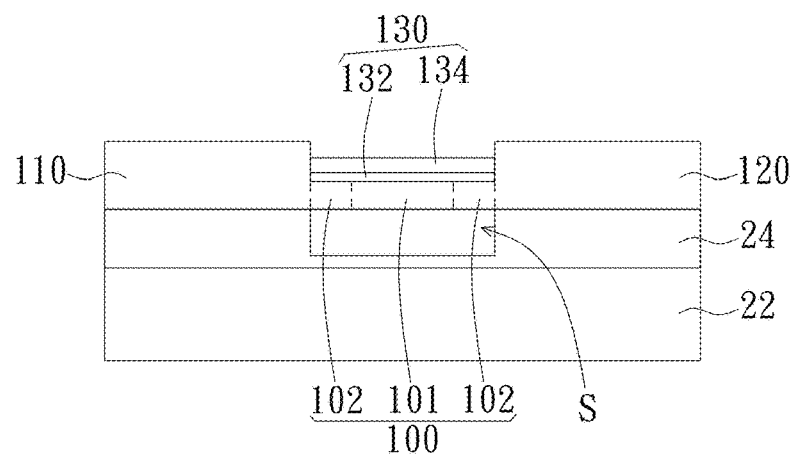

As shown in FIG. 11F, a passivation layer 320 is formed on the nanodevice. For example, a TEOS (tetraethyl orthosilicate) oxide layer is deposited on the silicon wafer. As shown in FIG. 11G and FIG. 11H, the passivation layer 320 is patterned to define the sensing region (i.e. the channel region). For example, the TEOS oxide layer is patterned to define the device channel 100. That is, photoresist 330 masks the source 110 and the drain 120, and the TEOS oxide layer is partially removed to expose the device channel 100. As shown in FIG. 11I, the insulation layer 24 under the device channel 100 is removed by wet etching to form the gap S under the device channel 100. For example, the oxide layer under the device channel 100 is removed in wet etching solution (such as HF solution) to form the gap S between the device channel 100 and the silicon substrate 22 (or the residual oxide layer), and therefore the suspending nanodevice is formed. Then, various sensing materials are selectively deposited on the lightly-doped regions 101 of the device channels 100 of different nano devices through localized Joule heating and CVD or ALD as described above, so the nano sensing chip with suspending nanodevices shown in FIG. 10A and FIG. 10B is formed.

Figure 12A:
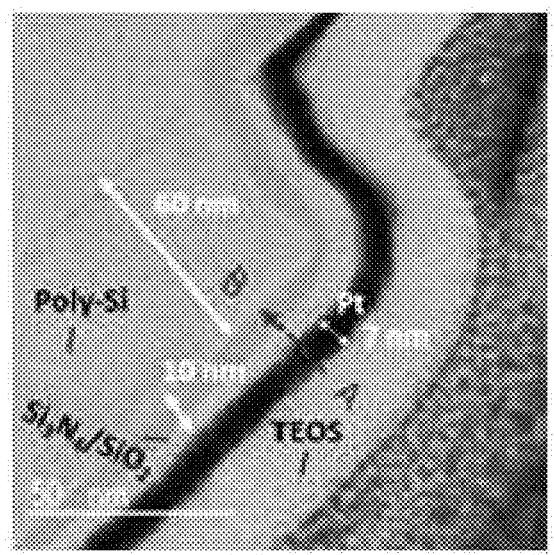
FIG. 12A presents a TEM image of selective deposition 10 nm Pt on the lightly-doped region of a 60 nm thick device channel of the nano sensing device.
Figure 12B:
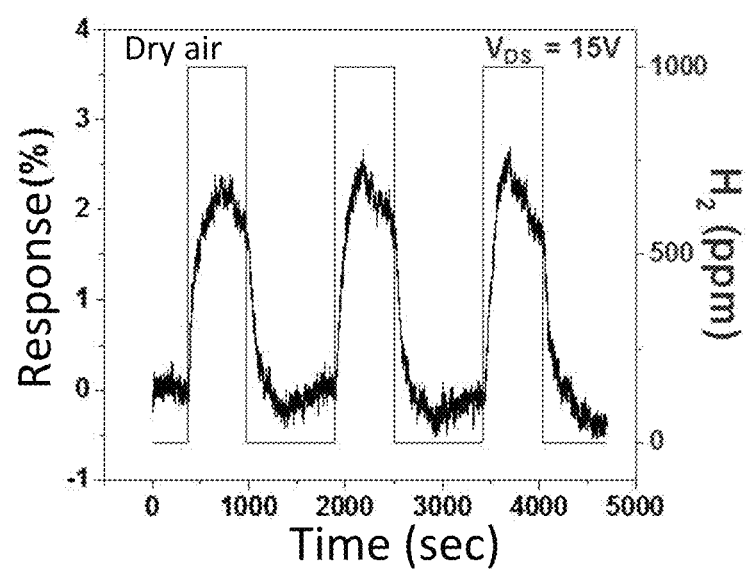
FIG. 12B shows the detection response of hydrogen (1000 ppm) of the nano sensing device (selective deposition of 10-nm Pt on channel) of FIG. 12A under device Joule self-heating.
Figure 13A:
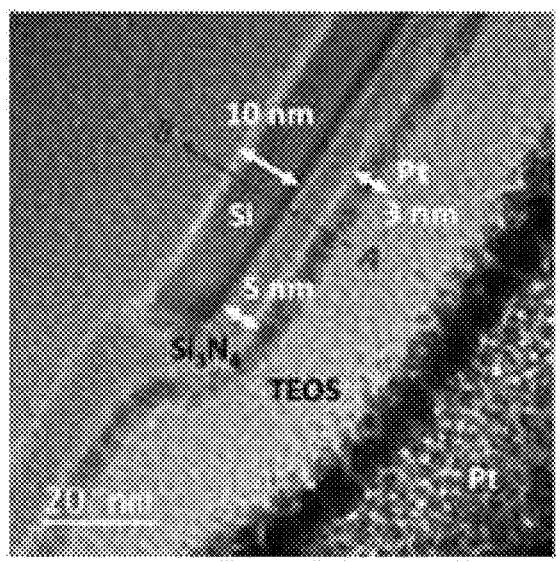
FIG. 13A presents a TEM image of selective deposition 3 nm Pt on the lightly-doped region of a 10 nm thick device channel of the nano sensing device.
Figure 13B:
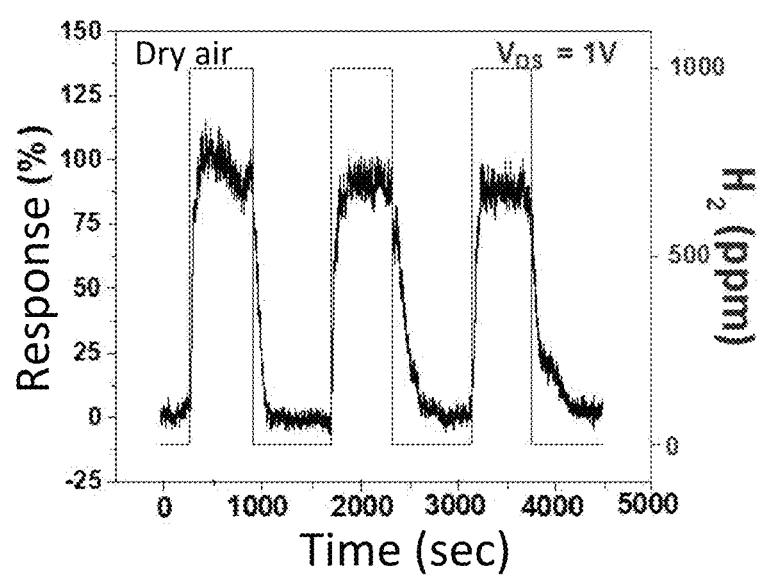
FIG. 13B shows the detection response of hydrogen (1000 ppm) of the nano sensing device of FIG. 13A under device Joule self-heating.

FIG. 12A presents a TEM image of selective deposition 10 nm Pt on the n-region of a 60 nm thick device channel of the nano sensing device. FIG. 12B shows the detection response of hydrogen (1000 ppm) of the nano sensing device of FIG. 12A under device Joule self-heating. As shown in FIG. 12A and FIG. 12B, for the nano sensing device having a device channel thickness of 60 nm, even though the nano sensing device is functioned under device Joule self-heating, 15V is required to obtain about 2.1% hydrogen response, and the power consumption for gas detection is about 16 nW. FIG. 13A presents a TEM image of selective deposition 3 nm Pt on the n-region of a 10 nm thick device channel of the nano sensing device. FIG. 13B shows the detection response of hydrogen (1000 ppm) of the nano sensing device of FIG. 13A under device Joule self-heating. As shown in FIG. 13A and FIG. 13B, for the nano sensing device having a device channel thickness of 10 nm, the nano sensing device is functioned under device Joule self-heating, merely 1V is required to obtain about 97% hydrogen response. Furthermore, as the volume of the n$^-$ region is reduced from 0.5 µm(W)×2 µm(L)×60 nm(T) in FIG. 12A to 0.35 µm(W)×1 µm(L)×10 nm(T) in FIG. 13A, the sensing voltage under device Joule self-heating is reduced from 15 V to 1V, and the sensing power consumption is also reduced from about 16 nW to about 1 nW.

In other words, the thickness of the device channel will greatly affect the sensitivity and the sensing power consumption. In an embodiment, the thickness of the device channel is preferably less than the Debye length to reduce the sensing power consumption under device Joule self-heating. The Debye length is a measure of a charge carrier's net electrostatic effect and how far its electrostatic effect persists (i.e. charge screening characteristics). For example, when the nanodevice is a n+/n−/n+ doped dual junction poly or single crystalline nanodevice, the device channel can be a nanobelt or a nanowire, and the thickness of the nanobelt or the diameter of the nanowire is preferably less than 20 nm.

Compared to the prior art, the invention provides a method for selective deposition of metal and/or metal oxide semiconductor on the lightly-doped regions of nanodevices through localized Joule heating and CVD or ALD, which is superior in applications of manufacturing nanodevices. Moreover, the method of the invention utilizes localized Joule heating and CVD or ALD to sequentially selectively deposit various sensing materials on specific regions by controlling the bias voltage of the specific regions, simplifying the manufacturing process without contaminating or damaging the previously deposited sensing materials. Moreover, invention selectively deposits different materials on specific regions of individual nanodevices, and the specific regions are highly sensitive in response to changes in surface potential. For gas-sensing applications, individual nanodevices can be functioned under device Joule self-heating to increase the surface temperature of the specific regions to optimize the reaction temperature (e.g. different reaction temperatures for different sensing materials and target gases), so as to achieve optimum gas detections. The nano sensing devices which function under device Joule self-heating can reduce the power consumption, which is generally greater than 25 mW/device for conventional gas sensing device. The nano sensing chip of the invention can be applied to sensing applications of multiple gases under device Joule self-heating to improve the device sensitivity and the device portability, suitable for ambient gas monitoring or gas sensing in human exhaled breath for disease diagnosis.

Although the preferred embodiments of present invention have been described herein, the above description is merely illustrative. The preferred embodiments disclosed will not limit the scope of the present invention. Further modification of the invention herein disclosed will occur to those skilled in the respective arts and all such modifications are deemed to be within the scope of the invention as defined by the appended claims.

What is claimed is:

1. A method for forming a nano sensing chip, comprising of a step:
    forming a nanodevice comprising a source, a drain, and a device channel with two ends capable of being biased, the device channel having a lightly-doped region capable of producing localized Joule heating; and
    in a chemical vapor deposition (CVD) system or an atomic layer deposition (ALD) system electrical-biasing the nanodevice so that the localized Joule heating modulates temperature of the lightly-doped region of the nanodevice enabling a selective deposition of a sensing material only on the lightly-doped region.

2. The method of claim 1, wherein the step of forming the nanodevice includes forming a plurality of nanodevices, and the step of enabling the selective deposition includes electrical-biasing the plurality of nanodevices in a first group so that the localized Joule heating modulates the temperature of the lightly-doped regions of the plurality of nanodevices in the first group enabling the selective deposition of the sensing material only on the lightly-doped regions of the plurality of nanodevices in the first group.

3. The method of claim 2, after the selective deposition of the sensing material on the lightly-doped region of the plurality of nanodevices in the first group is performed, further comprising:
    electrical-biasing the plurality of nanodevices in a second group so that the localized Joule heating modulates the temperature of the lightly-doped regions of the plurality of nanodevices in the second group enabling a selective deposition of another sensing material different from the sensing material only on the lightly-doped region of the plurality of nanodevices in the second group, wherein the device channels of the plurality of nanodevices in the first group are connected to a first common source and a first common drain, and the device channels of the plurality of nanodevices in the second group are connected to a second common source and a second common drain different from the first common source and the first common drain.

4. The method of claim 1, wherein the step of forming the nanodevice includes forming the device channel having the lightly-doped region between two heavily-doped regions.

5. The method of claim 1, wherein the sensing material is selected from the group consisting of platinum, palladium, tungsten, iridium, tin oxide, zinc oxide, tungsten oxide, aluminum oxide, and hafnium oxide.

6. The method of claim 1, further comprising forming a dielectric layer on the device channel, and the sensing material is deposited on the lightly-doped region with the dielectric layer interposed therebetween.

7. A method for forming a nano sensing chip, comprising:
    forming a plurality of nanodevices into a first group and a second group, each of the first group and the second group comprising one or more of the plurality of nanodevices, each of one or more of the plurality of nanodevices comprising a source, a drain, and a device channel with two ends capable of being biased, the channel device having a lightly-doped region capable of producing localized Joule heating;
    in a CVD system or an ALD system electrical-biasing the one or more of the plurality of nanodevices in the first group so that the localized Joule heating modulates temperature of the one or more lightly-doped regions of the one or more of the plurality of nanodevices in the first group enabling a selective deposition of a first sensing material only on the one or more lightly-doped regions of the one or more of the plurality of nanodevices in the first group; and
    after the first sensing material is deposited, electrical-biasing the one or more of the plurality of nanodevices in the second group so that the localized Joule heating modulates temperature of the one or more lightly-doped regions of the one or more of the plurality of nanodevices in the second group enabling a selective deposition of a second sensing material only on the one or more lightly-doped regions of the one or more of the plurality of nanodevices in the second group.

8. The method of claim 7, wherein the step of forming the plurality of nanodevices includes forming an array of the plurality of nanodevices, each of the device channels comprises the lightly-doped region between two heavily-doped regions.

9. The method of claim 7, wherein the first sensing material and the second sensing material are independently a metal material or a metal oxide semiconductor material.

10. The method of claim 9, wherein the metal material is selected from the group consisting of platinum, palladium, tungsten, and iridium, and wherein the metal oxide semiconductor material is selected from the group consisting of tin oxide, zinc oxide, tungsten oxide, aluminum oxide, and hafnium oxide.

11. The method of claim 7, wherein the device channels of the plurality of nanodevices in the first group are connected to a first common source and a first common drain, and the device channel of the one or more of the plurality of nanodevices in the second group are connected to a second common source and a second common drain different from the first common source and the first common drain.

12. The method of claim 7, wherein the first sensing material is different from the second sensing material, and the step of electrical-biasing the one or more of the plurality of nanodevices in the first group and the step of electrical-biasing the one or more of the plurality of nanodevices in the second group are performed by applying different bias voltages to the one or more of the plurality of nanodevices in the first group and in the second group.

13. The method of claim 7, wherein the first sensing material is different from the second sensing material, and the one or more of the plurality of nanodevices in the first group and the second group are configured to function under Joule self-heating at different working temperatures to simultaneously sense different target gases by the first sensing material and the second sensing material, respectively.

14. The method of claim 7, further comprising forming a dielectric layer on the device channel of the one or more of the plurality of nanodevices, and the first sensing material or the second sensing material is deposited on the one or more lightly-doped regions of the one or more of the plurality nanodevices in the first group or the second group with the dielectric layer interposed therebetween.

* * * * *